(12) United States Patent
Stroebeck et al.

(10) Patent No.: US 7,943,812 B2
(45) Date of Patent: May 17, 2011

(54) LAYERED ADHESIVE CONSTRUCT HAVING A MOULDABLE LAYER AS SKIN CONTACT SURFACE

(75) Inventors: Esben Stroebeck, Hoersholm (DK); Flemming Moss, Vedbaek (DK); Danuta Ciok, Nivaa (DK)

(73) Assignee: Colopast A/S, Humlebaek (DK)

( * ) Notice: Subject to any disclaimer, the term of this patent is extended or adjusted under 35 U.S.C. 154(b) by 316 days.

(21) Appl. No.: 12/087,117

(22) PCT Filed: Dec. 18, 2006

(86) PCT No.: PCT/DK2006/000722
§ 371 (c)(1),
(2), (4) Date: Jun. 26, 2008

(87) PCT Pub. No.: WO2007/076862
PCT Pub. Date: Jul. 12, 2007

(65) Prior Publication Data
US 2009/0171258 A1    Jul. 2, 2009

(30) Foreign Application Priority Data
Dec. 30, 2005    (DK) ................................ 2005 01851

(51) Int. Cl.
*A61F 13/00* (2006.01)
(52) U.S. Cl. ............... 602/54; 602/41; 602/52; 523/111

(58) Field of Classification Search ................... 602/41, 602/42, 52, 54; 604/332, 336, 342–345, 604/337–339; 523/111, 120, 105
See application file for complete search history.

(56) References Cited

U.S. PATENT DOCUMENTS

| | | | |
|---|---|---|---|
| 4,538,603 A | 9/1985 | Pawelchak et al. | |
| 6,451,883 B1 | 9/2002 | Chen et al. | |
| 6,509,391 B2 * | 1/2003 | Gothjaelpsen et al. | ........ 523/111 |

FOREIGN PATENT DOCUMENTS

| | | |
|---|---|---|
| EP | 0 413 250 A1 | 2/1991 |
| EP | 0 686 381 A1 | 12/1995 |
| EP | 1 527 789 A1 | 5/2005 |
| GB | 229074 | 2/1925 |
| WO | WO 94/15562 | 7/1994 |
| WO | WO 98/17212 | 4/1998 |
| WO | WO 98/17329 | 4/1998 |
| WO | WO 98/53771 | 12/1998 |
| WO | WO 2004/087004 A2 | 10/2004 |

* cited by examiner

*Primary Examiner* — Kim M Lewis
(74) *Attorney, Agent, or Firm* — Jacobson Holman PLLC

(57) ABSTRACT

A layered adhesive construct is provided having a backing layer, a first layer of a hydrocolloid adhesive, and a second layer of a hydrocolloid adhesive, where the first and second layers of hydrocolloid adhesives have different composition, and the second layer of hydrocolloid adhesive is interposed between the first layer of hydrocolloid adhesive and the backing layer. The first adhesive layer is a layer of moldable adhesive paste including hydrocolloids having a Strain Recovery below 45% and the second adhesive layer is a layer of hydrocolloid adhesive having a Strain Recovery above 55%.

20 Claims, No Drawings

LAYERED ADHESIVE CONSTRUCT HAVING A MOULDABLE LAYER AS SKIN CONTACT SURFACE

This is a national stage of PCT/DK2006/000722 filed Dec. 18, 2006 and published in English.

FIELD OF INVENTION

The present invention relates to a layered adhesive construct designed to be removably mounted on the skin, e.g. as a part of an ostomy device, or to be used in connection with fistulas, fecal incontinence management or wound care products and more particularly to such an appliance, which has the attributes of two or more types of pressure sensitive adhesives.

The present invention in particular relates to a layered adhesive construct comprising a mouldable adhesive paste as a skin contact adhesive.

BACKGROUND

In many cases, where the colon, the ileum or the urethra has been exposed surgically and the patient is left with an abdominal stoma, the effluents or waste products of the body, which are conveyed through these organs and discharged through the artificial orifice or opening and collected in a collection bag, the collection bag is usually adhered to the skin by means of an adhesive wafer or plate having an inlet opening for accommodating the stoma. Also, in connection with a fistula, the patient will also have to rely on an appliance to collect the bodily material emerging from such opening.

Often, an adhesive paste is used for filling the area between the stoma or fistula and a mounting gasket, ostomy washer and/or skin barrier or to build up an area on the abdomen around the stoma so as to provide a relatively flat and smooth surface onto which an appliance or skin barrier can be securely attached.

When used for adhering devices to the skin, the mouldability of the adhesive paste is very important in order to seal and fill in any irregularities and folds in the skin. On the other hand, a mouldable adhesive paste will, due to its higher degree of plasticity compared to elasticity or cohesiveness, have a tendency to flow away and leave openings between the device and the skin. Also, if a layer of adhesive paste with a backing layer is folded due to folds in the skin or otherwise, the adhesive paste may be pressed away from the backing, leaving parts of the backing with no adhesive, and thereby create leaks between the backing layer and the skin.

It has been found that by using a layered adhesive construction with a mouldable adhesive skin contact surface and a second layer of adhesive, which has a lower tendency to flow than the mouldable adhesive, between the backing layer and the mouldable adhesive, provides a construction with the advantages of a skin contact surface which is mouldable and a second layer providing a security against leakage.

It has also been found that the second adhesive layer may provide a certain rigidity to the layered construction which is an advantage with respect to preventing leakage and with respect to the tendency of leaving residues on the skin upon removal of the device.

Adhesive constructions comprising layers of hydrocolloid adhesives are well known in the art:

EP 1 527 789 A1 describes a construction comprising a film layer and at least two layers of hydrocolloid adhesives with different composition.

The prime object of the adhesive construction described therein is to provide a multi-layered adhesive medical appliance that has the attributes of a skin friendly wet tack pressure sensitive adhesive for use adjacent the skin, and a flexible, comfortable, moisture tolerant adhesive that resists degradation after sterilization, and is capable of creating a seal around the stoma in a controlled fashion, for use away from the skin.

It is described that a disadvantage of the known skin-friendly adhesives used adjacent to the skin is that they tend to be somewhat rigid when they become too thick. Thus according to this application, it is preferred that the adhesive layer adjacent to the skin is thinner than the more flexible, comfortable, moisture tolerant adhesive, which is use away from the skin.

EP 1 527 789 A1 also describes that one of the adhesive layers may be of a moldable hydrocolloid adhesive, but it is also apparent that the moldable adhesive layer in the construction is not the one of the two adhesive layers which is in contact with the skin, see paragraph 0033 of the reference.

EP 686 381 describes similar adhesive constructions with two layers of hydrocolloid adhesives with different composition. According to this patent application, the layer of adhesive securing the adhesive construction to the skin is composed of a skin friendly hydrocolloid containing adhesive which has a relatively low resistance to dissolution and/or disintegration when contacted by stomal fluids, whereas the other adhesive layer placed away from the skin is composed of a relatively soft, easy-deformable and extrudable adhesive sealant material that is more resistant to dissolution or disintegration by stomal fluids than the material of the skin contact adhesive. From the drawings it is clear that the adhesive layer adjacent to the skin is thinner than the adhesive layer placed away from the skin.

EP 413250 A1 describes an adhesive construction for use e.g. as part of an ostomy device, which comprises a backing layer and two layers of hydrocolloid adhesive. According to this document, both adhesive layers are in contact with the skin, the adhesive layer contacting the skin in the central part of the device being more than twice as thick as the adhesive layer contacting the skin in the peripheral portion of the construction.

U.S. Pat. No. 4,538,603 also describes and adhesive construction comprising two adhesive layers which may be of different composition, where the adhesive layer intended for skin contact is thicker than the adhesive layer placed away from the skin. The adhesive layer placed away from the skin is bonded to a foam layer carrying a film on the surface facing away from the adhesive layer. The adhesive construction described herein is useful for covering exudating wounds or ulcers. It is described that the relatively thick adhesive skin contact layer, is composed of ingredients permitting the adhesive construction to remain in place on the skin for several days. The water dispersible hydrocolloids, the water swellable cohesive strengthening agents and the hydratable polymers distributed throughout the adhesive layer gradually becomes hydrated over time. Eventually the adhesive layer becomes so hydrated that the construction can be removed without stripping or macerating the skin around the wound site. The relatively thick adhesive layer to be placed on the skin comprises thermoplastic elastomer, such as low molecular weight polyisobutylene, and hydrocolloids, water swellable cohesive strengthening agents and hydratable polymers, whereas the relatively thin adhesive layer placed away from the skin and bonded to the foam layer may also comprise plastizisers and tackifier.

WO 94/15562 describes adhesive constructions consisting of two adhesives, where one adhesive constitutes an island embedded in the other adhesive. It is described how the additional material unit which makes up the island may be of a less cohesive material and thereby more plastic, than the adhesive material making up the rest of the construct. The island may be a thicker or thinner layer than the other adhesive layer.

Layered adhesive constructions comprising a mouldable adhesive paste as the skin contact adhesive are described in GB 2290974, WO 98/17212 and WO98/53771. However, none of these constructions have a second adhesive layer between the layer of mouldable adhesive paste and the backing layer and in these constructions the paste is not used as the only adhesive means for attaching a medical device to the skin.

SUMMARY OF THE INVENTION

Thus, the present invention relates to a layered adhesive construct comprising a backing layer and a first and second layer of a hydrocolloid adhesive, where the first and second layer of hydrocolloid adhesive have different composition, and the second layer of hydrocolloid adhesive is interposed between the first layer of hydrocolloid adhesive and the backing layer and wherein the first adhesive layer is a layer mouldable adhesive paste comprising hydrocolloids having Strain Recovery below 45% when measured as described in the present application,
and the second adhesive layer is a layer of hydrocolloid adhesive having a Strain Recovery above 55% when measured as described in the present application.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

As described above the first adhesive layer of the adhesive construction of the invention is made of a mouldable hydrocolloid adhesive having a Strain Recovery below 45% when measured as described below. More preferred the Strain Recovery for the mouldable hydrocolloid adhesive is below 40%, or even more preferred below 35%.

Apart from the above-mentioned Strain Recovery characteristics, the mouldable hydrocolloid adhesive have good adhesion to the skin, good moisture handling properties and is skin friendly.

The second adhesive layer used according to the invention is suitably made of a hydrocolloid adhesive having a Strain Recovery above 55%. More preferred the Strain Recovery for the second adhesive layer is above 65% or even more preferred above 75%. The hydrocolloid adhesive used for the second adhesive layer has sufficient cohesive strength to avoid breakage or flow when folded into irregular areas of the skin and to help the first layer of adhesive to come off in essentially one piece when removed from the skin.

According to the present invention, the Strain Recovery is measured according to the method described below:

A plate of the adhesive material to be tested is pressed into a plate of 1 mm thickness. From this a round sample of 25 mm in diameter is cut out and placed in a RheoStress RS600 rheometer from Thermo Electron. The geometry applied is parallel 25 mm plates. The measurement is carried out at 32° C.

A shear deformation ($\gamma$) of 15% and 5% (total 20%) is applied in two steps in order to avoid overshoot in deformation and the 20% deformation is held for 60 seconds. (the overshoot of the deformation should not exceed 22%). The total time of the deformation should be less than 90 seconds. The stress is removed and the remaining elastic forces will recover some of the applied deformation. The resulting recovery of the deformation is measured after 1000 seconds.

The Strain Recovery is defined as the percentage recovery from large step strain and is calculated as follows:

Strain Recovery=$\gamma-\gamma_{1000}/\gamma$ where $\gamma$ is 0.20 and $\gamma_{1000}$ is the shear deformation after 1000 seconds, which may bee seen from the curve provided by the rheometer.

The first adhesive layer of the adhesive construct of the invention may be a mouldable hydrocolloid adhesive paste such as the ones described in WO 98/017329. In the mouldable adhesive pastes described herein, the combination of a styrene block copolymer having a relatively large content of di-block copolymer with a tackifying liquid constituent, and a waxy constituent has shown superior quality with respect to cohesion, giving the mass resistance against erosion and at the same time enabling the removal of the mass as an integrated unit without leaving residues at the skin.

The styrene block copolymer comprises triblock as well as diblock copolymer.

The styrene block copolymer used has a relatively low molecular weight and a high content of diblock copolymer. The content of diblock copolymer in the block copolymer renders the mouldable adhesive less elastic than a corresponding adhesive comprising a triblock copolymer due to a lesser degree of physical cross linking and thereby contributes to the plasticity and non-memory putty-like characteristics of the adhesive.

Accordingly, the mouldable adhesive used according to the invention suitably comprises: 1 to 20% by weight of a styrene block copolymer having a molecular weight determined by GPC (Gel Permeation Chromatography) of from 20.000 to 150.000, and having a content of diblock above 25%, 5 to 60% by weight of a tackifying liquid constituent in the form of a viscous polymeric material, which is compatible with the block copolymer; 1 to 10% by weight of a constituent which is like wax in nature or appearance; and one or more hydrocolloids.

According to one embodiment of the invention, the amount of styrene block copolymer in the mouldable adhesive paste is 1-10% w/w, or more preferred 5-10% w/w.

The block copolymer may be block copolymers such as SBS, SIS or SEBS copolymers, e.g., styrene and butadiene, isoprene or ethylenebutylene copolymers. The preferred copolymer is a SEBS (styrene-ethylenebutylene-styrene copolymer) having a content of di block component above 30% w/w, such as KRATON G1726 X or block copolymers with similar physical properties.

The tackifying viscous liquid constituent is preferably a viscous polymeric material being compatible with the block copolymer. The tackifying liquid may be a viscous liquid polybutylene or polyisobutylene and is preferably a saturated component, which cannot give rise to chemical cross-linking deteriorating the non-memory putty-like characteristics of the adhesive. The tackifying liquid component is preferred a polyisobutylene. The molecular weight of the viscous tackifying liquid is preferably from 10,000 to 120,000 when determined by GPC (Gel Permeation Chromatography).

The amount of tackifying liquid used for the mouldable adhesive is in one embodiment 15-60% w/w, or more preferred 30-40% w/w.

The mouldable mass of the invention may, if required, comprise a oily plasticizer for plasticizing SEBS and polyisobutylene/polybutylene in order to reduce the elasticity. Such oily plasticizer is suitably a viscous polymeric material having molecular weight from 300 to 10,000 when determined by GPC. The mouldable adhesive may thus comprise one or more constituents such as petroleum jelly in an amount of up to 20% by weight, polybutylene oil in an amount of up to 30% by weight and/or liquid paraffin in an amount of up to 30% by weight.

The mouldable adhesive useful according to the invention may comprise a tackifier increasing the adhesive properties of the composition in order to ensure a good contact between the appliance and the skin. Such a tackifier is preferably a hydrocarbon tackifier homogeneously distributed in the adhesive mass. The tackifier is preferably a terpene tackifier resin or a dicyclopentadiene tackifier resin. Especially preferred as hydrocarbon tackifier resin are polymers and copolymers of dicyclopentadiene, alpha-pinene and/or beta-pinene.

The waxy component may be a mineral wax or petroleum jelly and is most preferred microcrystalline wax, which is compatible with the preferred SEBS block copolymer.

Suitable hydrocolloids for incorporation into the adhesive compositions of the invention are selected from naturally occurring hydrocolloids, semisynthetic hydrocolloids and synthetic hydrocolloids.

The hydrocolloid may be cellulosed derivatives, such as sodium carboxymethylcellulose (CMC), hydroxyethylcellulose and methyl cellulose, pectin, gelatine, guar gum, karaya, locust bean gum, carrageenan, xanthan, or sodium or calcium alginate and/or sodium starch glycolate and/or polyvinylalcohol and/or polyethylene glycol.

It is preferred to use a combination of two or more hydrocolloids. It is especially preferred to use a combination of guar gum, pectin and hydroxyethylcellulose or of pectin, gelatine and CMC in order to achieve a good and firm gel The hydrocolloid will typically be present in an amount of from 20 to 70% by weight of the total composition in order to have a sufficient absorbent capacity and still retain the characteristics of the mouldable adhesive. More preferred, the total amount of hydrocolloids is from 30 to 60%, and most preferred the total amount of hydrocolloids is from 45 to 60% by weight.

For some purposes it is suitable also to include smaller amounts of a filler in the mass of the invention which may add to the cohesion and also contribute to the plasticity. Such filler may, e.g. be any filler known per se for ostomy or wound care purposes such as talc, calcium carbonate, china clay, zinc oxide or the like. Such filler may constitute up to 3-20% by weight of the composition.

Still further, the adhesive may optionally comprise further constituents such as emollients, disinfecting agents and/or bactericidal agents known per se for use for ostomy or wound care purposes.

In a preferred embodiment of the invention, the mouldable adhesive comprises 5-10% w/w styrene block copolymer, 30-40% w/w of a viscous liquid polyisobytylene, 2-5% w/w tackifier, 2-5% w/w microcrystalline wax and 45-55% w/w of hydrocolloids. Even more preferred the mouldable adhesive has a composition as described in example 2 below.

Other preferred mouldable adhesive are the ones described in example 1-13 in WO 98/017329 and the references cited in WO 98/017329.

The preparation of the mouldable adhesive mass may be carried out as described in WO 98/017329.

The second layer of hydrocolloid adhesive is suitable an adhesive such as the ones described in U.S. Pat. No. 6,451,883 The adhesive composition described in U.S. Pat. No. 6,451,883 comprises a homogeneous mixture of 5-20% of one or more styrene copolymers, 35-50% of one or more polybutenes, and 20-60% of one or more hydrocolloids.

It is preferred that the styrene copolymer is a styrene-butadiene-styrene block copolymer or a styrene-isoprene-styrene block copolymer. Preferably, one or more styrene-isoprene-styrene (SIS) block type copolymers are employed. Preferred block copolymers are KRATON D 1107, KRATON D-1161 NU or block copolymers with similar physical properties.

The amount of styrene block-copolymer is preferably from 5 to 20% of the total adhesive composition.

The polybutene component is suitably a polyisobutylene, such as Oppanol B10SFN, Oppanol B11SFN, Oppanol B12SFN, Oppanol B13SFN and Oppanol B15SFN. The molecular weight (Mn) of the polybutenes is preferably from 75,000 to 360,000.

The hydrocolloid(s) may be selected from the hydrocolloids described above for the mouldable adhesive layer. In a preferred embodiment, the adhesive composition used for the second adhesive layer also comprise a native starch, such as native potato starch, corn starch, pea starch or wheat starch, which is considerably less water absorbent than the hydrocolloids normally used in adhesives, e.g. the hydrocolloids mentioned above, but which provides the same rheology to the adhesive as hydrocolloids.

The backing layer may be a thin polymeric film, a non-woven fabric, or an open celled or closed celled foam layer optionally having its outer surface covered by a film.

Suitable material for thin polymeric films include polyolefins, such as polyethylene, polypropylene, ethylene acrylic acids, ethylene vinyl acetates, polyvinylchlorides, polyether sulfones, polyether ketones, polyurethanes etc. The polymeric films are suitably impermeable to liquid water and may have a varying degree of water vapour permeability. Suitable non-woven fabrics include those made from polyester fibres, polypropylene fibres, nylon fibres, composite olefin fibres, or cellulose The thickness of the backing layer may vary depending on the material it is made of. When the backing layer is a polymer film, such as a LDPE (low density polyethylene), LLDPE (linear low density polyethylene), EVA (ethylene vinyl acetate) and EBA (ethylene butyl acetate). The thickness of the backing layer is suitably 30-100 µm.

Preferred the backing layer is of a weldable material so that other items or devices may be welded onto the backing layer. Preferably, the backing layer is a weldable polymer film, such as a LLDPE (linear low density poly ethylene) having a thickness between 30 µm and 100 µm, preferably 40-70 µm.

The backing layer may also be a foam layer as described in U.S. Pat. No. 4,538,603.

In the layered adhesive construction according to the invention, the mouldable skin contact adhesive layer, i.e. the first adhesive layer is suitably thicker than the second adhesive layer. Preferably, the second adhesive layer is less than half as thick as the first adhesive layer.

According to one embodiment of the invention, the first adhesive layer is between 1-2.5 mm, preferably between 1.25-2.25 mm, more preferred 1.25-1.75 mm and most preferred about 1.5 mm.

The adhesive construct according to the invention may in one embodiment have a beveled peripheral portion. According to this embodiment, the adhesive construction has i) a central portion where the second adhesive layer has a thickness, which is less than half of the thickness of the first adhesive layer and ii) a beveled peripheral portion. In the beveled peripheral portion, the first adhesive layer may become thinner than the second adhesive layer, and may even disappear completely at some distance from the peripheral edge of the construct.

According to this embodiment of the invention, the first adhesive layer may be between 1-2.5 mm, preferably between 1.25-2.25 mm, more preferred 1.25-1.75 mm or most preferred about 1.5 mm in the central part of the adhesive construction.

The two adhesive layers may have the same area and shape, or the second layer may extend beyond the periphereral edge of the first adhesive layer, to be able to contact the skin in the area beyond the area where the first adhesive layer contacts the skin.

Suitably, the layered adhesive construct of the invention has a circular or ellipsoid shape.

In order to increase the length of the peripheral edge and thereby achieve a better attachment to the skin, the peripheral edge of the layered adhesive construct may be wave formed, and optionally the top point(s) of the waves form a circular or ellipsoid figure.

According to one embodiment of the invention, the layered adhesive construction has a pattern of indentations in the form of grooves in the surface provided with the backing layer. These grooves improve the flexibility of the adhesive construct and are formed in the first adhesive layer, leaving the backing layer and the second adhesive layer essentially intact. The depth of the grooves may correspond to the thickness of the first adhesive layer or be smaller than the thickness of the first adhesive layer.

According to one embodiment, the indentations extend radially from the center of the layered adhesive construct towards the periphery of the layered adhesive construct. Optionally the adhesive construct also has curvilinear indentations, which are crossing the radial indentations.

The use of indentations to improve the flexibility of an adhesive construct has been described in WO 04/087004.

The invention is illustrated more in detail in the below.

Materials and Methods

Kraton G1726 X from Kraton Polymers: Styrene-ethylenebutylene-styrene copolymer (SEBS) having a molecular weight of 45,000 as determined by GPC and a content of di-block copolymer of 70%.

Kraton D-1161 NU from Kraton Polymers
Elastoflex E1003D from Eastman Chemical
Indopol H-18000 polybutene from BP
Oppanol B 12 SFN polyisobutylene from BASF
Wax Total 40/60, microcrystalline wax from TOTAL.
Petroleum jelly: Vaselinum Album from Witco
Akucell AF 2881, carboxymethyl cellulose form AkzoNatrosol250 HX pharm, hydroxyethylcellulose from aqualon, Hercules Guar gum: Guar Gum FG 200 from Nordisk Gelatine
Pektin Pomosin LM 12CG Z from Copenhagen Pectin
Zinc Oxide: Zinkoxid Pharma from Hoechst AG
Native Potato Starch M4 from KMC
A Z mixer Type LKB 025 from Herman-Linden was used.

Experimental

EXAMPLE 1

Adhesive composition for the second adhesive layer:

| Ingredient | % w/w |
| --- | --- |
| Kraton D-1161 NU | 10 |
| Oppanol B 12 SFN | 40 |
| Akkucel AF2881 | 5 |
| Potato Starch | 45 |

EXAMPLE 2

Adhesive composition for the first adhesive layer:

| Ingredient | %-w/w |
| --- | --- |
| Kraton G 1726 X | 6.25 |
| Indopol H-1800 | 37.5 |
| Elastoflex E1003D | 3.125 |
| Total Wax 40/60 | 3.125 |
| Acucell AF 2881 | 5 |
| Natrosol 250HX pharm | 25 |
| Guar Gum FG 200 | 5 |
| Pektin Pomosin LM 12 | 14.5 |
| Zinkoxide | 0.5 |

EXAMPLE 3

The adhesives are produced on the conventional adhesive machinery (Z-blade ) and formed into adhesive layers between two release liners by heat pressing for 5 sec. at 90° C. The desired thickness are obtained by pressing the adhesive mass between two distance strips of 0,5 mm and 1,5 mm. These adhesives are then converted in to a layered construct by removing the release liner from the 0,5 mm thick second adhesive layer and applying a 55 µm LLDPE film, then removing the release liner of the first adhesive layer and laminating the two adhesives forming a 2 mm layered construct according to the invention. The construct is pressed and bevelled in a mould by heat press at 90° C. in 5 seconds in the heat press and cut out to the desired shape and size.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A layered adhesive construct to be applied onto skin comprising a backing layer, a first layer of a hydrocolloid adhesive that is applied to the skin, and a second layer of a hydrocolloid adhesive, said first and second layers of hydrocolloid adhesives having different composition, and the second layer of hydrocolloid adhesive being interposed between the first layer of hydrocolloid adhesive and the backing layer, said first adhesive layer being a layer of mouldable adhesive including hydrocolloids having a Strain Recovery below about 45%, and the second adhesive layer being a layer of hydrocolloid adhesive having a Strain Recovery above about 55%.

2. The layered adhesive construct according to claim 1 wherein the first adhesive layer is a layer of moldable adhesive paste comprising 1 to 20% by weight of a styrene block copolymer; 5 to 60% by weight of a tackifying liquid constituent in the form of a viscous polymeric material which is compatible with the block copolymer; 1 to 10% by weight of a constituent which is like wax in nature or appearance; and one or more hydrocolloids.

3. The layered adhesive construct according to claim 1 wherein the second adhesive layer is a layer of a hydrocolloid adhesive comprising from 5-20% of one or more styrene block copolymers, 35-50% of one or more polybutenes, and 20-60% of one or more hydrocolloids.

4. The layered adhesive construct according to claim 1 wherein a thickness of the second adhesive layer is less than half of a thickness of the first adhesive layer.

5. The layered adhesive construct according to claim 4 wherein the thickness of the first adhesive layer is between about 1.0 mm and about 2.5 mm.

6. The layered adhesive construct according to claim 4 wherein the thickness of the first adhesive layer is between about 1.25 mm and about 1.75 mm.

7. The layered adhesive construct according to claim 1 wherein the adhesive construct has i) a central portion where the second adhesive layer has a thickness which is less than half of a thickness of the first adhesive layer, and ii) a beveled peripheral portion.

8. The layered adhesive construct according to claim 7 wherein the thickness of the first adhesive layer is between about 1.0 mm and about 2.5 mm in the central portion of the layered adhesive construct.

9. The layered adhesive construct according to claim 7 wherein the thickness of the first adhesive layer is between about 1.25 mm and about 1.75 mm in the central portion of the layered adhesive construct.

10. The layered adhesive construct according to claim 1 wherein the backing layer is a film, a foam layer, a foam layer with a film layer, or a non-woven layer.

11. The layered adhesive construct according to claim 1 wherein the layered adhesive construct has a pattern of indentations in the form of grooves in the surface provided with the backing layer.

12. The layered adhesive construct according to claim 11 where the construct has indentations which extend radially from the center of the layered adhesive construct towards the periphery of the layered adhesive construct.

13. The layered adhesive construct according to claim 12 wherein the layered adhesive construct includes curvilinear indentations which cross the radial indentations.

14. The layered adhesive construct according to claim 1 wherein the layered adhesive construct has a circular or ellipsoid shape.

15. The layered adhesive construct according to claim 1 wherein the peripheral edge of the layered adhesive construct is wave formed, and the top point(s) of the waves form a circular or ellipsoid figure.

16. The layered adhesive construct according to claim 1 wherein the first and second layers of hydrocolloid adhesives are laminated to one another.

17. The layered adhesive construct according to claim 16 wherein a thickness of the second adhesive layer is less than half of a thickness of the first adhesive layer.

18. The layered adhesive construct according to claim 17 wherein the thickness of the first adhesive layer is between about 1.0 mm and about 2.5 mm.

19. The layered adhesive construct according to claim 17 wherein the thickness of the first adhesive layer is between about 1.25 mm and about 1.75 mm.

20. The layered adhesive construct according to claim 16 wherein the adhesive construct has i) a central portion where the second adhesive layer has a thickness which is less than half of a thickness of the first adhesive layer, and ii) a beveled peripheral portion.

* * * * *